United States Patent [19]

Gericke et al.

[11] Patent Number: 5,013,853
[45] Date of Patent: May 7, 1991

[54] CHROMAN DERIVATIVES

[75] Inventors: Rolf Gericke, Seeheim; Manfred Baumgarth; Ingeborg Lues, both of Darmstadt; Rolf Bergmann, Reichelsheim; Jacques De Peyer, Pfungstadt, all of Fed. Rep. of Germany

[73] Assignee: Merck Patent Gesellschaft MIT Beschränkter Haftung, Darmstadt, Fed. Rep. of Germany

[21] Appl. No.: 347,710

[22] Filed: May 5, 1989

[30] Foreign Application Priority Data

May 6, 1988 [DE]  Fed. Rep. of Germany ....... 3815504
Oct. 14, 1988 [DE]  Fed. Rep. of Germany ....... 3835011

[51] Int. Cl.$^5$ ........................................... C07D 311/22
[52] U.S. Cl. ..................... 549/401; 544/238; 544/315; 544/319; 544/408; 546/269; 548/517; 549/387; 549/399; 549/407; 549/396
[58] Field of Search ............... 549/399, 401, 387, 407, 549/396

[56] References Cited

U.S. PATENT DOCUMENTS

| | | | |
|---|---|---|---|
| 3,467,676 | 9/1969 | Jen et al. | 549/401 |
| 4,238,501 | 12/1980 | Kabbe et al. | 549/401 |
| 4,241,069 | 12/1980 | Buchler | 549/401 |
| 4,261,988 | 4/1981 | Widdig et al. | 549/401 |
| 4,479,007 | 10/1984 | Kabbe et al. | 549/401 |
| 4,486,428 | 12/1984 | Eggler | 514/253 |
| 4,510,152 | 4/1985 | Faruk | 549/399 |
| 4,687,779 | 8/1987 | Evans | 549/399 |
| 4,777,168 | 10/1988 | Kuhla | 514/396 |
| 4,841,076 | 6/1989 | Kitagawa | 549/401 |
| 4,968,819 | 11/1990 | Timar et al. | 549/401 |

FOREIGN PATENT DOCUMENTS

| | | | |
|---|---|---|---|
| 273262 | 6/1988 | European Pat. Off. | |
| 0135772 | 10/1979 | Japan | 549/387 |
| 1077066 | 7/1967 | United Kingdom | 549/401 |

OTHER PUBLICATIONS

Gabbutt et al., Chem. Abstr. vol. 103, Entry 37332f (1985).

Primary Examiner—Donald G. Daus
Attorney, Agent, or Firm—Millen, White & Zelano

[57] ABSTRACT

A compound of the formula:

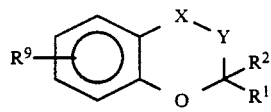

where in x-y is —CO—CH$_2$—, —COCR$^{10}$—, —CHOHCHR$^8$—, —CH=CR$^8$— or

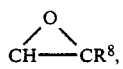

and R$^9$ is various, R$^1$ and R$^8$ are alkyl, R$_2$ is H or alkyl and R$^1$ and R$^2$ are alkylene, are disclosed as useful as intermediates for cardiovascular agents.

4 Claims, No Drawings

CHROMAN DERIVATIVES

SUMMARY OF THE INVENTION

The present invention relates to novel chroman derivatives of the formula I

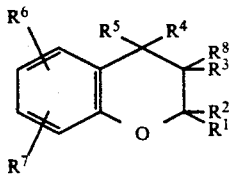

in which
R$^1$ and R$^8$ are in each case A,
R$^2$ is H or A,
R$^1$ and R$^2$ together are also alkylene having 3–6 C atoms,
R$^3$ is OH or OAc,
R$^4$ is H,
R$^3$ and R$^4$ together are also a bond,
R$^5$ is a pyridyl-oxy, pyridazinyl-oxy, pyrimidinyl-oxy, pyrazinyl-oxy, oxo-dihydro-pyridyl-oxy, oxo-dihydropyridazinyl-oxy, oxo-dihydro-pyrimidinyl-oxy, oxo-dihydropyrazinyl-oxy, 1H-2-pyridon-1-yl, 1H-6-pyridazinon-1-yl, 1H-2-pyrimidinon-1-yl, 1H-6-pyrimidinon-1-yl, 1H-2-pyrazinon-1-yl, 3H- or 5H-2-pyrrolinon-1-yl or 1H-2-thiopyridon-1-yl radical which is unsubstituted or monosubstituted or disubstituted by A, F, Cl, Br, I, OH, OA, OAc, NO$_2$, NH$_2$, AcNH, HOOC and/or AOOC, where these radicals may also be completely or partially hydrogenated,
R$^6$ and R$^7$ are in each case H, A, HO, AO, CHO, ACO, ACS, HOOC, AOOC, AO—CS, ACOO, A—CS—O, hydroxyalkyl having 1–6 C atoms, mercaptoalkyl having 1–6 C atoms, NO$_2$, NH$_2$, NHA, NA$_2$, CN, F, Cl, Br, I, CF$_3$, ASO, ASO$_2$, AO—SO, AO—SO$_2$, AcNH, AO—CO—NH, H$_2$NSO, HANSO, A$_2$NSO, H$_2$NSO$_2$, HANSO$_2$, A$_2$NSO$_2$, H$_2$NCO, HANCO, A$_2$NCO, H$_2$NCS, HANCS, A$_2$NCS, ASONH, ASO$_2$NH, AO-SONH, AOSO$_2$NH, ACO-alkyl, nitroalkyl, cyanoalkyl, A—C(=NOH) or A—C(=NNH$_2$),
A is alkyl having 1–6 C atoms,
alkyl is alkylene having 1–6 C atoms and
Ac is alkanoyl having 1–8 C atoms or aroyl having 7–11 C atoms,
and their salts.

Similar compounds are known from EP-A1-76,075 and EP-A1-173,848.

The invention was based on the object of finding novel compounds having useful properties, in particular those which can be used for the preparation of pharmaceuticals.

Upon further study of the specification and appended claims, further objects and advantages of this invention will become apparent to those skilled in the art.

It has been found that the compounds of the formula I and their physiologically acceptable salts possess, combined with good tolerability, useful pharmacological properties. Thus, they show effects on the cardiovascular system, it being possible to observe a selective effect on the cardiovascular system at lower doses and a hypotensive effect at higher doses. In the coronary system, for example, decreases in resistance and increases in flow occur, with the influence on the heart rate remaining low. Furthermore, the compounds show a relaxant effect on various smooth muscle organs (e.g., gastrointestinal tract, respiratory system, and uterus). The effects of the compounds can be determined with the aid of methods which are known per se, as are given, for example in EP-A1-173,848 or AU-A-45,547/85 (Derwent Farmdoc No. 86081769) and by K. S. Meesmann et al., Arzneimittelforschung 25 (11), 1975, 1770–1776. Suitable experimental animals are, for example, mice, rats, guinea pigs, dogs, cats, apes, or pigs.

The compounds can, therefore, be used as active medicament compounds in human and veterinary medicine. In addition, they can be used as intermediates for the preparation of further active medicament compounds.

In the formulae given, A is a preferably unbranched alkyl group having 1–6, preferably 1–4, in particular 1, 2 or 3 C atoms, in detail preferably methyl, in addition preferably ethyl, propyl, isopropyl, butyl, isobutyl, and furthermore preferably sec.-butyl, tert.-butyl, pentyl, isopentyl (3-methylbutyl), hexyl or isohexyl (4-methylpentyl).

If R$^1$ and R$^2$ together are alkylene, the alkylene group is preferably unbranched, in detail preferably —(CH$_2$)$_n$—, where n is 3, 4, 5 or 6.

The group "alkyl" preferably stands for —CH$_2$— or —CH$_2$CH$_2$—.

Ac is preferably alkanoyl having 1–6, in particular 1, 2, 3 or 4 C atoms, in detail preferably formyl or acetyl, furthermore preferably propionyl, butyryl, isobutyryl, pentanoyl or hexanoyl, and in addition preferably benzoyl, o-, m- or p-toluyl, 1- or 2-naphthoyl.

R$^1$ and R$^2$ are preferably each alkyl, in particular each methyl or ethyl, preferably each methyl.

R$^3$ and R$^4$ are preferably together a bond. If R$^4$ is H, R$^3$ is preferably OH, O—CHO or O—COCH$_3$.

R$^5$ is preferably unsubstituted 1H-2-pyridon-1-yl, 2-hydroxy-4-pyridyl-oxy, 6-hydroxy-3-pyridazinyl-oxy, 1,6-dihydro-1-methyl- or 1,6-dihydro-1-ethyl-6-oxo-3-pyridazinyl-oxy, furthermore 2-, 3- or 4-pyridyl-oxy, 3-hydroxy-1H-6-pyridazinon-1-yl or 1H-4-hydroxy-2-pyridon-1-yl, in addition preferably unsubstituted 1H-2-pyrazinon-1-yl, 1H-6-pyridazinon-1-yl, 4,5-dihydro-1H-6-pyridazinon-1-yl, 1H-2-pyrimidinon-1-yl, 1H-6-pyrimidinon-1-yl, 3H- or 5H-pyrrolinon-1-yl or 1H-2-thiopyridon-1-yl. If R$^5$ is an unsubstituted pyridone or thiopyridone ring, this ring is preferably monosubstituted in the 3-, 4- or 5-position or disubstituted in the 3-and 5-position. Particularly preferred substituents are OH, NO$_2$ and NH$_2$, in addition AOOC, OA, Cl, Br and NHCOCH$_3$, particularly preferred substituted radicals R$^5$ in detail being 4-, hydroxy; in addition 3-, 5- and 6-hydroxy-, 3-, 4-, 5- or 6-methoxy-, 3-, 4-, 5- or 6-acetoxy-, 3-, 5-or 6-chloro-, 3-or 5-nitro-, 3- or 5-amino-, 3- or 5-methoxycarbonyl-, 3- or 5-ethoxycarbonyl-, 3- or 5-acetamido-, 3,5-dichloro-, 3,5-dibromo-, 3-chloro-5-nitro-, 3-nitro-5-chloro-, 3-bromo-5-nitro-, 3-nitro-5-bromo-, 3,5-dinitro-, 3-chloro-5-amino-, 3-amino-5-chloro-, 3-bromo-5-amino-, 3-amino-5-bromo-, 3-chloro-5-acetamido-, 3-acetamido-5-chloro-, 3-bromo-5-acetamido-and 3-acetamido-5-bromo-1H-2-pyridon-1-yl or -1H-2-thiopyridon-1-yl, 1H-4- or 1H-5-hydroxy-6-pyridazinon-1-yl, 1H-3-, 1H-4-or 1H-5-methoxy-6-pyridazinon-1-yl, 1H-3-, 1H-4- or 1H-5-ethoxycarbonyl-6-pyridazinon-1-yl, 1H-4-, 1H-5- or 1H-6-hydroxy- 2-pyrimidinon-1-yl, 1H-2- or 1H-4-hydroxy-6-pyrimidinon-1-yl.

$R^5$ can in addition preferably be: 3,4-dihydro-1H-2-pyridon-1-yl, 2,3-dihydro-6H-2-pyridon-1-yl, 5,6-dihydro-1H-2-pyridon-1-yl, 2-piperidinon-1-yl, 2,3-dihydro-1H-6-pyridazinon-1-yl, 1,2-dihydro-5H-6-pyridazinon-1-yl, 4,5-dihydro-1H-6-pyridazinon-1-yl, 2,3,4,5-tetrahydro-1H-6-pyridazinon-1-yl, 3,4-dihydro-1H-2-pyrimidinon-1-yl, 1,6-dihydro-3H-2-pyrimidinon-1-yl, 5,6-dihydro-1H-2-pyrimidinon-1-yl, 3,4,5,6-tetrahydro-1H-2-pyrimidinon-1-yl, 2,3-dihydro-1H-6-pyrimidinon-1-yl, 1,2-dihydro-5H-6-pyrimidinon-1-yl, 4,5-dihydro-1H-6-pyrimidinon-1-yl, 2,3,4,5-tetrahydro-1H-6-pyrimidinon-1-yl, 3,4-dihydro-1H-2-pyrazinon-1-yl, 1,6-dihydro-3H-2-pyrazinon-1-yl, 5,6-pyrazinon-1-yl, 1,6-dihydro-3H-2-pyrazinon-1-yl, 5,6-dihydro-1H-2-pyrazinon-1-yl, 3,4,5,6-tetrahydro-1H-2-pyrazinon-1-yl, 2-pyrrolidinon-1-yl, 3,4-dihydro-1H-2-thiopyridon-1-yl, 2,3-dihydro-6H-2-thiopyridon-1-yl, 5,6-dihydro-1H-2-thiopyridon-1-yl.

In $R^6$ and $R^7$, the following are preferably:

A: methyl, and in addition ethyl;
AO: methoxy, and in addition ethoxy;
ACO: acetyl, and in addition propionyl;
ACS: thioacetyl, and in addition thiopropionyl;
AOOC: methoxycarbonyl, and in addition ethoxycarbonyl;
AO-CS: methoxy-thiocarbonyl, and in addition ethoxy-thiocarbonyl;
ACOO: acetoxy, and in addition propionoxy;
ACSO: thio(no)acetoxy, and in addition thio(no)propionoxy;
hydroxyalkyl: hydroxymethyl or 1- or 2-hydroxyethyl;
mercaptoalkyl: mercaptomethyl or 1- or 2-mercaptoethyl;
NHA: methylamino, and in addition ethylamino;
$NA_2$: dimethylamino, and in addition diethylamino;
ASO: methylsulfinyl, and in addition ethylsulfinyl;
$ASO_2$: methylsulfonyl, and in addition ethylsulfonyl;
AO-SO: methoxy-sulfinyl, and in addition ethoxysulfinyl;
$AO-SO_2$: methoxy-sulfonyl, and in addition ethoxysulfonyl;
Ac-NH: acetamido, and in addition formamido, propionamido or benzamido;
AO-CO-NH: methoxycarbonylamino, and in addition ethoxycarbonylamino;
HANSO: methylaminosulfinyl, and in addition ethylaminosulfinyl
$A_2NSO$: dimethylaminosulfinyl, and in addition diethylaminosulfinyl;
$HANSO_2$: methylaminosulfonyl, and in addition ethylaminosulfonyl;
$A_2NSO_2$: dimethylaminosulfonyl, and in addition diethylaminosulfonyl;
HANCO: N-methylcarbamoyl, and in addition N-ethylcarbamoyl;
$A_2NOC$: N,N-dimethylcarbamoyl, and in addition N,N-diethylcarbamoyl;
HANCS: N-methyl-thiocarbamoyl, and in addition N-ethyl-thiocarbamoyl;
$A_2NCS$: N,N-dimethyl-thiocarbamoyl, and in addition N,N-diethyl-thiocarbamoyl;
ASONH: methylsulfinylamino, and in addition ethylsulfinylamino;
$ASO_2NH$: methylsulfonylamino, and in addition ethylsulfonylamino;
AOSONH: methoxysulfinylamino, and in addition ethoxysulfinylamino;
$AOSO_2NH$: methoxysulfonylamino, and in addition ethoxysulfonylamino;
ACO-alkyl: 2-oxopropyl, 2-oxobutyl, 3-oxobutyl, 3-oxopentyl;
Nitroalkyl: nitromethyl, 1- or 2-nitroethyl;
Cyanoalkyl: cyanomethyl, 1- or 2-cyanoethyl;
A—C(=NOH): 1-oximinoethyl, and in addition 1-oximinopropyl;
A—C(=$NNH_2$): 1-hydrazinoethyl, and in addition 1-hydrazinopropyl.

The radicals $R^6$ and $R^7$ are preferably in the 6- and 7-position of the chroman system. However, they may also be in the 5- and 6-, 5- and 7-, 5- and 8-, 6- and 8- and 7- and 8-position.

One of the radicals $R^6$ and $R^7$ is preferably H, whereas the other is different from H. This other radical is preferably in the 6-position, but also in the 5-, 7- or 8-position, and is preferably CN or $NO_2$, in addition preferably CHO, ACO (in particular acetyl), AOOC (in particular methoxycarbonyl or ethoxycarbonyl), ACOO (in particular acetoxy), and furthermore preferably F, Cl, Br, I, $CF_3$, $H_2NCO$, $H_2NCS$ or $NH_2$.

Accordingly, the invention in particular relates to those compounds of the formula I in which at least one of the radicals mentioned has one of the previously mentioned preferred meanings. Some preferred groups of compounds can be expressed by the formulae Ia to Ii below, which correspond to the formula I and in which the radicals not designated in more detail have the meaning indicated in the formula I, in which however
in Ia $R^1$ and $R^2$ are each A;
in Ib $R^1$ and $R^2$ are each $CH_3$;
in Ic $R^1$ and $R^2$ together are alkylene having 3–6 atoms;
in Id $R^5$ is 1H-2-pyridon-1-yl, 2-pyrrolidinon-1-yl, 2-hydroxy-4-pyridyl-oxy-, 6-hydroxy-3-pyridazinyl-oxy, 1,6-dihydro-1-methyl-6-oxo-3-pyridazinyl-oxy or 1,6-dihydro-1-ethyl-6-oxo-3-pyridazinyl-oxy;
in Ie $R^5$ is 2-hydroxy-4-pyridyl-oxy, 6-hydroxy-3-pyridazinyl-oxy, 1,6-dihydro-1-methyl-6-oxo-3-pyridazinyl-oxy or 1,6-dihydro-1-ethyl-6-oxo-3-pyridazinyl-oxy;
in If $R^5$ is 6-hydroxy-3-pyridazinyl-oxy;
in Ig
  $R^1$ and $R^2$ are each $CH_3$ and
  $R^5$ is 1H-2-pyridon-1-yl, 2-pyrrolidinon-1-yl, 2-hydroxy-4-pyridyl-oxy, 6-hydroxy-3-pyridazinyl-oxy, 1,6-dihydro-1-methyl-6-oxo-3-pyridazinyl-oxy or 1,6-dihydro-1-ethyl-6-oxo-3-pyridazinyl-oxy;
in Ih
  $R^1$ and $R^2$ are each $CH_3$ and
  $R^5$ is 2-hydroxy-4-pyridyl-oxy, 6-hydroxy-3-pyridazinyl-oxy, 1,6-dihydro-1-methyl-6-oxo-3-pyridazinyl-oxy or 1,6-dihydro-1-ethyl-6-oxo-3-pyridazinyl-oxy;
in Ii
  $R^1$ and $R^2$ are each $CH_3$ and
  $R^5$ is 6-hydroxy-3-pyridazinyl-oxy.

Compounds of the formulae I' and Ia' to Ii' are furthermore preferred which correspond to the formulae I and Ia to Ii, but in which in each case $R^3$ is additionally OH, OCHO or $OCOCH_3$ and $R^4$ is H.

Compounds of the formulae I" and Ia" to Ii" are furthermore preferred which correspond to the formulae I and Ia to Ii, but in which in each case $R^3$ and $R^4$ together are additionally a bond.

Compounds of the formulae I, I', I'', Ia to Ii, Ia' to Ii', and Ia'' to Ii'' are in addition preferred, in which in each case additionally (a)
$R^6$ is different from H and
$R^7$ is H;

(b)
$R^6$ is different from H and is in the 6-position and
$R^7$ is H;

(c)
$R^6$ is $NO_2$, CN, CHO, ACO, HOOC, AOOC, ACOO, F, Cl, Br, I, $CF_3$, $H_2NCO$, $H_2NCS$ or $NH_2$ and
$R^7$ is H;

(d)
$R^6$ is $NO_2$, CN, CHO, ACO, HOOC, AOOC, ACOO, F, Cl, Br, I, $CF_3$, $H_2NCO$, $H_2NCS$ or $NH_2$ and is in the 6-position and
$R^7$ is H;

(e)
$R^6$ is $NO_2$, CN, CHO, $CH_3CO$, $CH_3OOC$, $C_2H_5OOC$ or $CH_3COO$ and
$R^7$ is H;

(f)
$R^6$ is $NO_2$, CN, CHO, $CH_3CO$, $CH_3OOC$, $C_2H_5OOC$ or $CH_3COO$ and is in the 6-position and
$R^7$ is H;

(g)
$R^6$ is $NO_2$ or CN and
$R^7$ is H;

(h)
$R^6$ is $NO_2$ or CN and is in the 6-position and
$R^7$ is H;

(i)
$R^6$ is CN and
$R^7$ is H;

(j)
$R^6$ is CN and is in the 6-position and
$R^7$ is H.

Compounds of the formulae I, I', I'', Ia to Ii, Ia' to Ii', Ia'' to Ii'' and the remaining groups of compounds previously indicated as preferred are particularly preferred, in which $R^8$ is additionally $CH_3$.

Otherwise, the radicals $R^1$ to $R^8$, A, "alkyl" and Ac above and below have the meanings given in formula I, if not expressly stated otherwise.

The invention in addition relates to a process for the preparation of chroman derivatives of the formula I, characterized in that a 3,4-epoxychroman of the formula II

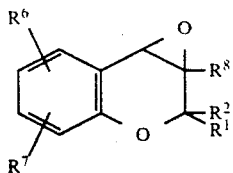

in which
$R^1$, $R^2$, $R^6$, $R^7$ and $R^8$ have the meanings given in formula I, is reacted with a compound of the formula III $R^5$—H      III in which $R^5$ has the meaning given in formula I or with one of its reactive derivatives
and/or in that a compound of the formula I, in which $R^3$ is OH and $R^4$ is H, is dehydrated and/or in that one or more of the radicals $R^3$, $R^5$, $R^6$ and/or $R^7$ are converted into other radicals $R^3$, $R^5$, $R^6$ and/or $R^7$ in a compound of the formula I and/or in that a basic compound of the formula I is converted into one of its acid addition salts by treating with an acid.

The compounds of the formula I are otherwise prepared by methods which are known per se, as are described in the literature (for example in the standard works such as Houben-Weyl, Methoden der organischen Chemie (Methods of Organic Chemistry), Georg-Thieme Verlag, Stuttgart; Organic Reactions, John Wiley & Sons, Inc., New York; and in the abovementioned patent applications), in particular under reaction conditions which are known and suitable for the reactions mentioned. In this case, use can also be made of variants which are known per se but which are not mentioned in more detail here.

The starting materials may also be formed, if desired, in situ in such a way that they are not isolated from the reaction mixture, but immediately reacted further to give the compounds of the formula I.

Preferably, the compounds of the formula I are prepared by reacting compounds of the formula II with compounds of the formula III, preferably in the presence of an inert solvent at temperatures between about 0° and 150°.

The starting materials of the formula III are usually known. If they are not known, they can be prepared by methods which are known per se. The starting materials of the formula II are obtainable by reacting 2-hydroxyacetophenones of the formula 2—HO—$R^6R^7C_5H_2$—$COCH_3$ with ketones of the formula Va,

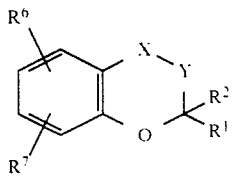

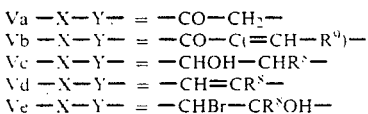

condensing with aldehydes of the formula $R^9$—CHO ($R^9$=alkyl having 1–5 C atoms) to give 3-alkylidene-4-chromanones of the formula Vb, reducing, for example with $NaBH_4$, to give 3-alkyl-4-chromanols of the formula Vc, dehydrating, for example with p-toluenesulfonic acid, to give chromenes of the formula Vd and oxidizing, for example with 3-chloroperbenzoic acid. The last-mentioned oxidation can also be carried out in a number of steps. Thus, for example, the bromohydrins of the formula Ve can initially be prepared using N-bromosuccinimide in aqueous solution and these can subsequently be treated with a base, for example sodium hydroxide solution.

The chromenes of the formula Vd can also be obtained by condensation of salicylaldehydes of the formulation of 2—HO—$R^6R^7C_6H_2$—CHO with ketones of the formula $R^1$—CO—$CH_2$—$R^8$ to give hydroxyketones of the formula 2—HO—$R^6R^7C_6H_2$—CH=C-$R^8$—CO—$R^1$, reaction with organolithium compounds of the formula $R^2$—Li and subsequent hydrolysis to give diols of the formula 2—HO—$R^6R^7C_6$-

$H_2-CH=CR^8-CR^1R^2-OH$, and cyclization with elimination of water.

Reactive derivatives of III which are suitable are the corresponding salts, for example the Na or K salts, which can also be formed in situ. Different products of formula I can be formed by the reaction of II with III, dependent in particular from the structure of the starting materials and from the reaction conditions.

For instance, the formation of compounds of formula I containing an oxygen bridge ($R^5$=unsubstituted or substituted pyridyl-oxy, pyridazinyl-oxy, pyrimidinyl-oxy, pyrazinyl-oxy, oxo-dihydro-pyridyl-oxy, oxo-dihydropyridazinyl-oxy, oxo-dihydro-pyrimidinyl-oxy or oxo-dihydro-pyrazinyl-oxy) is favored if the compound III contains at least one OH group as a substituent in addition to the lactame or lactime group and/or if the reaction is carried out under relatively mild conditions, e.g., in the presence of a weak base such as pyridine in an alcohol. For instance, from 2,2,3-trimethyl-3,4-epoxy-6-cyano-chromane ("IIa") and 1H-2-pyridone with NaH in DMSO there are formed predominantly 2,2,3-trimethyl-4-(1H-2-pyridon-1-yl)-6-cyano-2H-chromene ("A") and 2,2,3-trimethyl-4-(1H-2-pyridon-1-yl)-6-cyano-chroman-3-ol ("B"), whereas with pyridine in ethanol there are formed about equal parts of "B" and 2,2,3-trimethyl-4-(2-pyridyl-oxy)-6-cyano-chroman-3-ol. From 2,4-dihydroxypyridine (=4-Hydroxy-1H-2-pyridone) and IIa in pyridine/ethanol there are formed 2,2,3-trimethyl-4-(2-hydroxy-4-pyridyl-oxy)-6-cyano-chroman-3-ol and 2,2,3-trimethyl-4-(4-hydroxy-1H-2-pyridon-1-yl)-6-cyano-chroman-3-ol in a weight ratio of about 9:1. In each single case optimal reaction conditions can be worked out easily. The reaction products can be separated and isolated without difficulties, e.g., by crystallization and/or chromatography.

It is preferable to work in the presence of a base. Suitable bases are, for example, hydroxides, hydrides and also amides of alkali metals or alkaline earth metals, such as NaOH, KOH, Ca(OH)$_2$, NaH, KH, CaH$_2$, NaNH$_2$, KNH$_2$, and in addition organic bases such as triethylamine or pyridine which can also be used in excess and then simultaneously serve as the solvent.

Suitable inert solvents are, in particular, alcohols such as methanol, ethanol, isopropanol, n-butanol or tert.-butanol; ethers such as diethyl ether, diisopropyl ether, tetrahydrofuran or dioxane; glycol ethers such as ethylene glycol monomethyl ether or ethylene glycol monoethyl ether (methyl glycol or ethyl glycol), ethylene glycol dimethyl ether (diglyme); ketones such as acetone or butanone; nitriles such as acetonitrile; nitro compounds such as nitromethane or nitrobenzene; esters such as ethyl acetate; amides such as dimethylformamide (DMF), dimethylacetamide or hexamethylphosphoramide; sulfoxides such as dimethyl sulfoxide (DMSO); chlorinated hydrocarbons such as dichloromethane, chloroform, trichloroethylene, 1,2-dichloroethane or carbon tetrachloride; hydrocarbons such as benzene, toluene or xylene. Mixtures of these solvents with one another are furthermore suitable.

The epoxide II can also be prepared in situ, for example by the action of a base on the corresponding bromohydrin Ve.

A compound of the formula I, in which $R^3$=OH and $R^4$=H can be converted into a compound of the formula I, in which $R^3$ and $R^4$ are together a bond, by treating with a dehydrating agent. This is carried out, for example, by the action of one of the bases mentioned, for example NaOH, KOH or NaH, in one of the solvents mentioned, for example tetrahydrofuran, dioxane or DMSO, at temperatures between 0° and 150°.

Furthermore, one or more of the radicals $R^3$, $R^5$, $R^6$ and/or $R^7$ can be converted into other radicals $R^3$, $R^5$, $R^6$ and/or $R^7$ in a compound of the formula I.

For example, it is possible to replace an H atom by a halogen atom by means of a halogenation or by a nitro group by means of a nitration and/or to reduce a nitro group to an amino group and/or to alkylate or acylate an amino or hydroxyl group and/or to convert a cyano group (for example with HCl in water/methanol at 20°–100°) into a carboxyl group or (for example with Raney nickel in water/acetic acid/pyridine in the presence of sodium phosphate) into a formyl group or (for example with KOH in tert.-butanol) into a carbamoyl group or (for example with H$_2$S in pyridine/triethylamine) into a thiocarbamoyl group and/or to convert a substituted or unsubstituted 1H-2-pyridon-1-yl radical (for example with P$_2$S$_5$ or with Lawesson reagent in toluene) into the corresponding 1H-2-thiopyridon-1-yl radical.

Nitration is carried out under customary conditions, for example using a mixture of concentrated HNO$_3$ and concentrated H$_2$SO$_4$ at temperatures between 0° and 30°. If at least one of the substituents $R^6$ and $R^7$ is an electronegative group such as CN or NO$_2$, the nitration predominantly takes place at the radical $R^5$; otherwise mixtures are usually obtained in which the nitro groups are on the radical $R^5$ or on the chroman ring.

This applies analogously to the halogenation which can be carried out, for example, using elemental chlorine or bromine in one of the customary inert solvents at temperatures between about 0° and 30°.

A primary or secondary amino group and/or an OH group can be converted into the corresponding secondary or tertiary amino group and/or alkoxy group by treating with alkylating agents. Suitable alkylating agents are, for example, compounds of the formulae A—Cl, A—Br or A—I or corresponding sulfuric acid or sulfonic acid esters, such as methyl chloride, bromide or iodide, dimethyl sulfate or methyl p-toluenesulfonate. In addition, for example, one or two methyl groups can be introduced with formaldehyde in the presence of formic acid. The alkylation is preferably carried out in the presence or absence of one of the inert solvents mentioned, for example DMF, at temperatures between about 0° and about 120°, in which case a catalyst can also be present, preferably a base such as potassium tert.-butoxide or NaH.

Suitable acylating agents for the acylation of amino or hydroxyl groups are preferably the halides (for example chlorides or bromides) or anhydrides of carboxylic acids of the formula Ac—OH, for example acetic anhydride, propionyl chloride, isobutyryl bromide, formic acid/acetic anhydride and benzoyl chloride. The addition of a base such as pyridine or triethylamine during the acylation is possible. The acylation is preferably carried out in the presence or absence of an inert solvent, for example a hydrocarbon such as toluene, a nitrile such as acetonitrile, an amide such as DMF or an excess of a tertiary base such as pyridine or triethylamine, at temperatures between about 0° and about 160°, preferably between 20° and 120°. Formylation is also carried out using formic acid in the presence of pyridine.

A base of the formula I can be converted into the respective acid addition salt using an acid. Acids which give physiologically acceptable salts are particularly suitable for this reaction. Thus, inorganic acids can be used, for example sulfuric acid, nitric acid, hydrohalic acids such as hydrochloric acid or hydrobromic acid, phosphoric acids such as orthophosphoric acid, sulfamic acid, and in addition organic acids, in particular aliphatic, alicyclic, araliphatic, aromatic or heterocyclic monobasic or polybasic carboxylic, sulfonic or sulfuric acids, for example formic acid, acetic acid, propionic acid. pivalic acid, diethylacetic acid, malonic acid, succinic acid, pimelic acid, fumaric acid, maleic acid, lactic acid, tartaric acid, malic acid, benzoic acid, salicylic acid, 2- or 3-phenylpropionic acid, citric acid, gluconic acid, ascorbic acid, nicotinic acid, isonicotinic acid, methanesulfonic or ethanesulfonic acid, ethanedisulfonic acid, 2-hydroxyethanesulfonic acid, benzenesulfonic acid, p-toluenesulfonic acid, naphthalene monosulfonic and disulfonic acids, and laurylsulfuric acid. Salts with physiologically unacceptable acids, for example picrates, can be used for purifying the compounds of the formula I.

The compounds of the formula I may possess one or more chiral centres. They can therefore be obtained during their preparation as racemates or also, if optically active starting materials are used, in optically active form. If the compounds have two or more chiral centres, they may be obtained during synthesis as mixtures of racemates from which the individual racemates can be isolated in pure form, for example by recrystallizing from inert solvents. Thus, for example, compounds of the formula I in which $R^1=R^2$, $R^3=OH$ and $R^4=H$ have two chiral centres; during preparation by reaction of II with III, however, very predominantly only one racemate having the trans-position of the substituents $R^3=OH$ and $R^5$ is formed. Racemates obtained can, if desired, be separated mechanically or chemically into their enantiomers by methods known per se. Thus, diastereomers can be formed from the racemate by reaction with an optically active resolving agent. Suitable resolving agents for basic compounds of the formula I are, for example, optically active acids, such as the D- and L-forms of tartaric acid, dibenzoyltartaric acid, diacetyltartaric acid, camphorsulfonic acids, mandelic acid, malic acid or lactic acid. Carbinols (I, $R^3=OH$) can in addition be esterified and then resolved with the aid of chiral acylating reagents, for example D- or L-α-methylbenzyl isocyanate (cf. EP-A1-120,428). The different forms of the diastereomers can be separated in a manner known per se, for example by fractional crystallization, and the enantiomers of the formula I can be liberated in a manner known per se from the diastereomers. Resolution of enantiomers is in addition carried out by chromatography on optically active support materials.

The compounds of the formula I and their physiologically acceptable salts can be used for the production of pharmaceutical preparations, in particular in nonchemical ways. In this connection, they can be brought into a suitable form for administration together with at least one solid, liquid and/or semi-liquid excipient or auxiliary and, if desired, in combination with one or more further active compound(s).

The invention in addition relates to agents, in particular pharmaceutical preparations, containing at least one compound of the formula I and/or one of its physiologically acceptable salts.

These preparations can be used as medicaments in human or veterinary medicine. Suitable excipients are organic or inorganic substances which are suitable for enteral (for example oral), parenteral or topical administration and which do not react with the novel compounds, for example water, vegetable oils, benzyl alcohols, polyethylene glycols, glycerol triacetate, gelatin, carbohydrates such as lactose or starch, magnesium stearate, talc or petroleum jelly. Tablets, coated tablets, capsules, syrups, elixirs or drops are used in particular for oral administration, suppositories are used in particular for rectal administration, solutions, preferably oily or aqueous solutions, and in addition suspensions, emulsions or implants are used in particular for parenteral administration, and ointments, creams or powders are used in particular for topical application. The new compounds can also be lyophilized and the lyophilizates obtained used, for example, for the production of injection preparations. The preparations mentioned can be sterilized and/or can contain auxiliaries such as lubricants, preservatives, stabilizers and/or wetting agents, emulsifiers, salts for influencing the osmotic pressure, buffer substances, colorants and flavourings and/or aromatizers. They can, if desired, also contain one or more further active compounds, for example one or more vitamins.

The compounds of the formula I and their physiologically acceptable salts can be administered to humans or animals, in particular mammals such as apes, dogs, cats, rats or mice and can be used in the therapeutic treatment of the human or animal body and also in the control of diseases, in particular in the therapy and/or prophylaxis of disturbances of the cardiovascular system, in particular decompensated cardiac insufficiency, angina pectoris, peripheral or cerebral vessel disorders, and disease conditions which are connected with high blood pressure, and in addition disorders which are connected with changes in the non-vascular musculature. for example asthma or urinary incontinence.

In this connection, the substances according to the invention are usually administered analogously to known antianginals or hypotensives, for example nicorandil or cromakalim. preferably in doses between about 0.01 and 5 mg, in particular between 0.02 and 0.5 mg per dose unit. The daily dose is preferably between about 0.0001 and 0.1, in particular between 0.0003 and 0.01 mg/kg of body weight. The specific dose for each particular patient depends, however, on a variety of factors, for example on the efficacy of the specific compound employed, on the age, body weight, the general state of health, sex, on the food, on the time and route of administration, on the excretion rate, medicament combination and severity of the particular disease to which the therapy applies. Oral administration is preferred.

The invention also relates to the novel intermediates of the formula IV

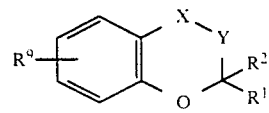

IV in which
—X—Y— denotes (a) —CO—CH$_2$—, (b) —CO—CR$^{10}$— (c) —CHOH—CHR$^6$, (d) —CH=CR$^6$—, or

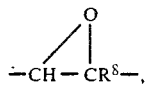

$R^9$ denotes CHO, ACO, AOOC, $NO_2$, CN, Br, $H_2$NCO, or $H_2$NCCS, wherein A is as defined above, and $R^{10}$ denotes alkylidene having 1–6 C atoms, and $R^1$, $R^2$, and $R^8$ have the meaning given in Formula I.

These intermediates can be used to form compounds of Formula I.

These novel intermediates can be prepared according to the instructions in Example 1 or analogously thereto.

In the following examples, "customary working up" means: water is added, if necessary, and the mixture is extracted using an organic solvent such as ethyl acetate; the organic phase is separated off, dried over sodium sulfate, filtered, and evaporated; and the residue is purified by chromatography and/or crystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire texts of all applications, patents and publications, if any, cited above and below, and of corresponding applications P Nos. 38 15 504.4 and P 38 35 011.4, filed in West Germany on May 6, 1988, and Oct. 14, 1988, respectively, are hereby incorporated by reference.

A mixture of 21.5 g of 2,2,3-trimethyl-3,4-epoxy-6-cyanochroman ("IIa"), 9.5 g of 1H-2-pyridone ("pyridone"), 3 g of an 80% dispersion of NaH in paraffin oil and 600 ml of DMSO is stirred at 20° for 16 hours and poured into water, and the mixture is extracted using ethyl acetate. The extract is evaporated and the residue is chromatographed on silica gel. 2,2,3-Trimethyl-4-(1H-2-pyridon-1-yl)-6-cyano-2H-chromene ("A"; m.p. 212°) is eluted using dichloromethane, then 2,2,3-trimethyl-4-(1H-2-pyridon-1-yl)-6-cyano-chroman-3-ol ("B"; m.p. 185°–186°) using ethyl acetate.

Preparation of the starting material:

(a) A mixture of 81 g of 3-acetyl-4-hydroxybenzonitrile, 48 ml of acetone, 11.8 ml of pyrrolidine and 300 ml of toluene is allowed to stand at 20° for 1 hour, then boiled for 2 hours in a water separator and cooled. After customary working up, 2,2-dimethyl-6-cyano-4-chromanone is obtained, m.p. 119°–120°.

(b) A solution of 24 g of the chromanone, 12 g of paraformaldehyde and 24 ml of piperidine in 300 ml of ethanol is heated at 70° for 3 hours and evaporated. The residue is taken up in dichloromethane/petroleum ether 1:1, the mixture is filtered through silica gel and evaporated, and 2,2-dimethyl-3-methylene-6-cyano-4-chromanone is obtained as an unstable oil.

(c) 6 g of $NaBH_4$ are added to a solution of 25 g of the above chromanone in 500 ml of methanol, and the mixture is stirred at 20° for 1 hour and evaporated. After customary working up, 2,2,3-trimethyl-6-cyano-4-chromanol is obtained as an oily isomer mixture.

(d) A solution of 27 g of the above mixture and 1.2 g of p-toluenesulfonic acid in 400 ml of toluene is boiled in a water separator for 3 hours. The mixture is evaporated, the residue is dissolved in dichloromethane/petroleum ether 1:1, the solution is filtered through silica gel and evaporated again, and 2,2,3-trimethyl-6-cyano-2H-chromene is obtained, m.p. 55°.

(e) A solution of 6.4 g of m-chloroperbenzoic acid in 40 ml of dichloromethane is added dropwise with stirring to a solution of 6.8 g of the above chromene in 100 ml of dichloromethane. The mixture is stirred for 16 hours, filtered, dilute sodium hydroxide solution is added, and the mixture is worked up as usual and 2,2,3-trimethyl-3,4-epoxy-6-cyanochroman (IIa) is obtained, m.p. 118°.

The enantiomers of IIa are obtainable by reaction of 2,2,3-trimethyl-6-cyano-2H-chromene with N-bromosuccinimide to yield 2,2,3-trimethyl-3-bromo-6-cyano-chroman-4-ol, esterification with (+)- or (−)-camphanic acid chloride to give the diastereomeric camphanic acid esters, separation of the enantiomers by crystallization or chromatography and treatment with base, thereby effecting saponification and cyclization to the enantiomeric epoxide IIa.

The following are obtained analogously:

2,2,3-trimethyl-4-(1H-2-thiopyridon-1-yl)-6-cyano-2H-chromene 2,2,3-trimethyl-4-(1H-2-thiopyridon-1-yl)-6-cyano-chroman-3-ol 2,2,3-trimethyl-4-(1H-3-chloro-2-pyridon-1-yl)-6-cyano-2H-chromene 2,2,3-trimethyl-4-(1H-3-chloro-2-pyridon-1-yl)-6-cyano-chroman-3-ol 2,2,3-trimethyl-4-(1H-5-chloro-2-pyridon-1-yl)-6-cyano-2H-chromene 2,2,3-trimethyl-4-(1H-5-chloro-2-pyridon-1-yl)-6-cyano-chroman-3-ol 2,2,3-trimethyl-4-(1H-6-chloro-2-pyridon-1-yl)-6-cyano-2H-chromene 2,2,3-trimethyl-4-(1H-6-chloro-2-pyridon-1-yl)-6-cyano-chroman-3-ol 2,2,3-trimethyl-4-(1H-3-hydroxy-2-pyridon-1-yl)-6-cyano-2H-chromene 2,2,3-trimethyl-4-(1H-3-hydroxy-2-pyridon-1-yl)-6-cyano-chroman-3-ol 2,2,3-trimethyl-4-(1H-4-hydroxy-2-pyridon-1-yl)-6-cyano-2H-chromene 2,2,3-trimethyl-4-(1H-4-hydroxy-2-pyridon-1-yl)-6-cyano-chroman-3-ol 2,2,3-trimethyl-4-(1H-5-hydroxy-2-pyridon-1-yl)-6-cyano-2H-chromene 2,2,3-trimethyl-4-(1H-5-hydroxy-2-pyridon-1-yl)-6-cyano-chroman-3-ol 2,2,3-trimethyl-4-(1H-3-methoxy-2-pyridon-1-yl)-6-cyano-2H-chromene 2,2,3-trimethyl-4-(1H-3-methoxy-2-pyridon-1-yl)-6-cyano-chroman-3-ol 2,2,3-trimethyl-4-(1H-3-acetoxy-2-pyridon-1-yl)-6-cyano-2H-chromene 2,2,3-trimethyl-4-(1H-3-acetoxy-2-pyridon-1-yl)-6-cyano-chroman-3-ol 2,2,3-trimethyl-4-(1H-3-nitro-2-pyridon-1-yl)-6-cyano-2H-chromene 2,2,3-trimethyl-4-(1H-3-nitro-2-pyridon-1-yl)-6-cyano-chroman-3-ol 2,2,3-trimethyl-4-(1H-5-nitro-2-pyridon-1-yl)-6-cyano-2H-chromene
2,2,3-trimethyl-4-(1H-5-nitro-2-pyridon-1-yl)-6-cyano-chroman-3-ol
2,2,3-trimethyl-4-(1H-3-amino-2-pyridon-1-yl)-6-cyano-2H-chromene
2,2,3-trimethyl-4-(1H-3-amino-2-pyridon-1-yl)-6-cyano-chroman-3-ol
2,2,3-trimethyl-4-(1H-5-amino-2-pyridon-1-yl)-6-cyano-2H-chromene
2,2,3-trimethyl-4-(1H-5-amino-2-pyridon-1-yl)-6-cyano-chroman-3-ol
2,2,3-trimethyl-4-(1H-3-acetamido-2-pyridon-1-yl)-6-cyano-2H-chromene
2,2,3-trimethyl-4-(1H-3-acetamido-2-pyridon-1-yl)-6-cyano-chroman-3-ol
2,2,3-trimethyl-4-(1H-5-acetamido-2-pyridon-1-yl)-6-cyano-2H-chromene
2,2,3-trimethyl-4-(1H-5-acetamido-2-pyridon-1-yl)-6-cyano-chroman-3-ol
2,2,3-trimethyl-4-(1H-3-carboxy-2-pyridon-1-yl)-6-cyano-2H-chromene
2,2,3-trimethyl-4-(1H-3-carboxy-2-pyridon-1-yl)-6-cyano-chroman-3-ol
2,2,3-trimethyl-4-(1H-5-carboxy-2-pyridon-1-yl)-6-cyano-2H-chromene
2,2,3-trimethyl-4-(1H-5-carboxy-2-pyridon-1-yl)-6-cyano-chroman-3-ol
2,2,3-trimethyl-4-(1H-3,5-dichloro-2-pyridon-1-yl)-6-cyano-2H-chromene
2,2,3-trimethyl-4-(1H-3,5-dichloro-2-pyridon-1-yl)-6-cyano-chroman-3-ol
2,2,3-trimethyl-4-(1H-3,5-dibromo-2-pyridon-1-yl)-6-cyano-2H-chromene
2,2,3-trimethyl-4-(1H-3,5-dibromo-2-pyridon-1-yl)-6-cyano-chroman-3-ol
2,2,3-trimethyl-4-(1H-3-chloro-5-nitro-2-pyridon-1-yl)-6-cyano-2H-chromene
2,2,3-trimethyl-4-(1H-3-chloro-5-nitro-2-pyridon-1-yl)-6-cyano-chroman-3-ol
2,2,3-trimethyl-4-(1H-3-nitro-5-chloro-2-pyridon-1-yl)-6-cyano-2H-chromene
2,2,3-trimethyl-4-(1H-3-nitro-5-chloro-2-pyridon-1-yl)-6-cyano-chroman-3-ol
2,2,3-trimethyl-4-(1H-3-bromo-5-nitro-2-pyridon-1-yl)-6-cyano-2H-chromene
2,2,3-trimethyl-4-(1H-3-bromo-5-nitro-2-pyridon-1-yl)-6-cyano-chroman-3-ol
2,2,3-trimethyl-4-(1H-3-nitro-5-bromo-2-pyridon-1-yl)-6-cyano-2H-chromene
2,2,3-trimethyl-4-(1H-3-nitro-5-bromo-2-pyridon-1-yl)-6-cyano-chroman-3-ol
2,2,3-trimethyl-4-(1H-3,5-dinitro-2-pyridon-1-yl)-6-cyano-2H-chromene
2,2,3-trimethyl-4-(1H-3,5-dinitro-2-pyridon-1-yl)-6-cyano-chroman-3-ol
2,2,3-trimethyl-4-(1H-3-chloro-5-amino-2-pyridon-1-yl)-6-cyano-2H-chromene
2,2,3-trimethyl-4-(1H-3-chloro-5-amino-2-pyridon-1-yl)-6-cyano-chroman-3-ol
2,2,3-trimethyl-4-(1H-3-amino-5-chloro-2-pyridon-1-yl)-6-cyano-2H-chromene
2,2,3-trimethyl-4-(1H-3-amino-5-chloro-2-pyridon-1-yl)-6-cyano-chroman-3-ol
2,2,3-trimethyl-4-(1H-3-bromo-5-amino-2-pyridon-1-yl)-6-cyano-2H-chromene
2,2,3-trimethyl-4-(1H-3-bromo-5-amino-2-pyridon-1-yl)-6-cyano-chroman-3-ol
2,2,3-trimethyl-4-(1H-3-amino-5-bromo-2-pyridon-1-yl)-6-cyano-2H-chromene
2,2,3-trimethyl-4-(1H-3-amino-5-bromo-2-pyridon-1-yl)-6-cyano-chroman-3-ol
2,2,3-trimethyl-4-(1H-3-chloro-5-acetamido-2-pyridon-1-yl)-6-cyano-2H-chromene
2,2,3-trimethyl-4-(1H-3-chloro-5-acetamido-2-pyridon-1-yl)-6-cyano-chroman-3-ol
2,2,3-trimethyl-4-(1H-3-acetamido-5-chloro-2-pyridon-1-yl)-6-cyano-2H-chromene
2,2,3-trimethyl-4-(1H-3-acetamido-5-chloro-2-pyridon-1-yl)-6-cyano-chroman-3-ol
2,2,3-trimethyl-4-(1H-3-bromo-5-acetamido-2-pyridon-1-yl)-6-cyano-2H-chromene
2,2,3-trimethyl-4-(1H-3-bromo-5-acetamido-2-pyridon-1-yl)-6-cyano-chroman-3-ol
2,2,3-trimethyl-4-(1H-3-acetamido-5-bromo-2-pyridon-1-yl)-6-cyano-2H-chromene
2,2,3-trimethyl-4-(1H-3-acetamido-5-bromo-2-pyridon-1-yl)-6-cyano-chroman-3-ol
2,2,3-trimethyl-4-(1H-2-pyridon-1-yl)-6-nitro-2H-chromene
2,2,3-trimethyl-4-(1H-2-pyridon-1-yl)-6-nitro-chroman-3-ol, m.p. 220°–222°
2,2,3-trimethyl-4-(1H-2-thiopyridon-1-yl)-6-nitro-2H-chromene
2,2,3-trimethyl-4-(1H-2-thiopyridon-1-yl)-6-nitro-chroman-3-ol
2,2,3-trimethyl-4-(1H-3-chloro-2-pyridon-1-yl)-6-nitro-chromene
2,2,3-trimethyl-4-(1H-3-chloro-2-pyridon-1-yl)-6-nitro-chroman-3-ol
2,2,3-trimethyl-4-(1H-5-chloro-2-pyridon-1-yl)-6-nitro-2H-chromene
2,2,3-trimethyl-4-(1H-5-chloro-2-pyridon-1-yl)-6-nitro-chroman-3-ol
2,2,3-trimethyl-4-(1H-6-chloro-2-pyridon-1-yl)-6-nitro-2H-chromene
2,2,3-trimethyl-4-(1H-6-chloro-2-pyridon-1-yl)-6-nitro-chroman-3-ol
2,2,3-trimethyl-4-(1H-3-hydroxy-2-pyridon-1-yl)-6-nitro-2H-chromene
2,2,3-trimethyl-4-(1H-3-hydroxy-2-pyridon-1-yl)-6-nitro-chroman-3-ol
2,2,3-trimethyl-4-(1H-4-hydroxy-2-pyridon-1-yl)-6-nitro-2H-chromene
2,2,3-trimethyl-4-(1H-4-hydroxy-2-pyridon-1-yl)-6-nitro-chroman-3-ol
2,2,3-trimethyl-4-(1H-5-hydroxy-2-pyridon-1-yl)-6-nitro-2H-chromene
2,2,3-trimethyl-4-(1H-5-hydroxy-2-pyridon-1-yl)-6-nitro-chroman-3-ol
2,2,3-trimethyl-4-(1H-3-methoxy-2-pyridon-1-yl)-6-nitro-2H-chromene
2,2,3-trimethyl-4-(1H-3-methoxy-2-pyridon-1-yl)-6-nitro-chroman-3-ol
2,2,3-trimethyl-4-(1H-3-acetoxy-2-pyridon-1-yl)-6-nitro-2H-chromene
2,2,3-trimethyl-4-(1H-3-acetoxy-2-pyridon-1-yl)-6-nitro-chroman-3-ol
2,2,3-trimethyl-4-(1H-3-nitro-2-pyridon-1-yl)-6-nitro-2H-chromene
2,2,3-trimethyl-4-(1H-3-nitro-2-pyridon-1-yl)-6-nitro-chroman-3-ol
2,2,3-trimethyl-4-(1H-5-nitro-2-pyridon-1-yl)-6-nitro-2H-chromene
2,2,3-trimethyl-4-(1H-5-nitro-2-pyridon-1-yl)-6-nitro-chroman-3-ol 2,2,3-trimethyl-4-(1H-3-amino-2-pyridon-1-yl)-6-nitro-2H-chromene
2,2,3-trimethyl-4-(1H-3-amino-2-pyridon-1-yl)-6-nitro-chroman-3-ol
2,2,3-trimethyl-4-(1H-5-amino-2-pyridon-1-yl)-6-nitro-2H-chromene
2,2,3-trimethyl-4-(1H-5-amino-2-pyridon-1-yl)-6-nitro-chroman-3-ol
2,2,3-trimethyl-4-(1H-3-acetamido-2-pyridon-1-yl)-6-nitro-2H-chromene
2,2,3-trimethyl-4-(1H-3-acetamido-2-pyridon-1-yl)-6-nitro-chroman-3-ol
2,2,3-trimethyl-4-(1H-5-acetamido-2-pyridon-1-yl)-6-nitro-2H-chromene
2,2,3-trimethyl-4-(1H-5-acetamido-2-pyridon-1-yl)-6-nitro-chroman-3-ol
2,2,3-trimethyl-4-(1H-3-carboxy-2-pyridon-1-yl)-6-nitro-2H-chromene
2,2,3-trimethyl-4-(1H-3-carboxy-2-pyridon-1-yl)-6-nitro-chroman-3-ol
2,2,3-trimethyl-4-(1H-5-carboxy-2-pyridon-1-yl)-6-nitro-2H-chromene
2,2,3-trimethyl-4-(1H-5-carboxy-2-pyridon-1-yl)-6-nitro-chroman-3-ol
2,2,3-trimethyl-4-(1H-3,5-dichloro-2-pyridon-1-yl)-6-nitro-2H-chromene
2,2,3-trimethyl-4-(1H-3,5-dichloro-2-pyridon-1-yl)-6-nitro-chroman-3-ol
2,2,3-trimethyl-4-(1H-3,5-dibromo-2-pyridon-1-yl)-6-nitro-2H-chromene
2,2,3-trimethyl-4-(1H-3,5-dibromo-2-pyridon-1-yl)-6-nitro-chroman-3-ol
2,2,3-trimethyl-4-(1H-3-chloro-5-nitro-2-pyridon-1-yl)-6-nitro-2H-chromene
2,2,3-trimethyl-4-(1H-3-chloro-5-nitro-2-pyridon-1-yl)-6-nitro-chroman-3-ol
2,2,3-trimethyl-4-(1H-3-nitro-5-chloro-2-pyridon-1-yl)-6-nitro-2H-chromene
2,2,3-trimethyl-4-(1H-3-nitro-5-chloro-2-pyridon-1-yl)-6-nitro-chroman-3-ol
2,2,3-trimethyl-4-(1H-3-bromo-5-nitro-2-pyridon-1-yl)-6-nitro-2H-chromene
2,2,3-trimethyl-4-(1H-3-bromo-5-nitro-2-pyridon-1-yl)-6-nitro-chroman-3-ol
2,2,3-trimethyl-4-(1H-3-nitro-5-bromo-2-pyridon-1-yl)-6-nitro-2H-chromene
2,2,3-trimethyl-4-(1H-3-nitro-5-bromo-2-pyridon-1-yl)-6-nitro-chroman-3-ol
2,2,3-trimethyl-4-(1H-3,5-dinitro-2-pyridon-1-yl)-6-nitro-2H-chromene
2,2,3-trimethyl-4-(1H-3,5-dinitro-2-pyridon-1-yl)-6-nitro-chroman-3-ol
2,2,3-trimethyl-4-(1H-3-chloro-5-amino-2-pyridon-1-yl)-6-nitro-2H-chromene
2,2,3-trimethyl-4-(1H-3-chloro-5-amino-2-pyridon-1-yl)-6-nitro-chroman-3-ol
2,2,3-trimethyl-4-(1H-3-amino-5-chloro-2-pyridon-1-yl)-6-nitro-2H-chromene
2,2,3-trimethyl-4-(1H-3-amino-5-chloro-2-pyridon-1-yl)-6-nitro-chroman-3-ol
2,2,3-trimethyl-4-(1H-3-bromo-5-amino-2-pyridon-1-yl)-6-nitro-2H-chromene
2,2,3-trimethyl-4-(1H-3-bromo-5-amino-2-pyridon-1-yl)-6-nitro-chroman-3-ol
2,2,3-trimethyl-4-(1H-3-amino-5-bromo-2-pyridon-1-yl)-6-nitro-2H-chromene
2,2,3-trimethyl-4-(1H-3-amino-5-bromo-2-pyridon-1-yl)-6-nitro-chroman-3-ol
2,2,3-trimethyl-4-(1H-3-chloro-5-acetamido-2-pyridon-1-yl)-6-nitro-2H-chromene
2,2,3-trimethyl-4-(1H-3-chloro-5-acetamido-2-pyridon-1-yl)-6-nitro-chroman-3-ol
2,2,3-trimethyl-4-(1H-3-acetamido-5-chloro-2-pyridon-1-yl)-6-nitro-2H-chromene
2,2,3-trimethyl-4-(1H-3-acetamido-5-chloro-2-pyridon-1-yl)-6-nitro-chroman-3-ol
2,2,3-trimethyl-4-(1H-3-bromo-5-acetamido-2-pyridon-1-yl)-6-nitro-2H-chromene
2,2,3-trimethyl-4-(1H-3-bromo-5-acetamido-2-pyridon-1-yl)-6-nitro-chroman-3-ol
2,2,3-trimethyl-4-(1H-3-acetamido-5-bromo-2-pyridon-1-yl)-6-nitro-2H-chromene
2,2,3-trimethyl-4-(1H-3-acetamido-5-bromo-2-pyridon-1-yl)-6-nitro-chroman-3-ol
2,2,3-trimethyl-4-(1H-2-pyridon-1-yl)-6-acetyl-2H-chromene
2,2,3-trimethyl-4-(1H-2-pyridon-1-yl)-6-acetyl-chroman-3-ol
2,2,3-trimethyl-4-(1H-2-pyridon-1-yl)-6-methoxycarbonyl-2H-chromene
2,2,3-trimethyl-4-(1H-2-pyridon-1-yl)-6-methoxycarbonyl-chroman-3-ol
2,2,3-trimethyl-4-(1H-2-pyridon-1-yl)-6-ethoxycarbonyl-2H-chromene
2,2,3-trimethyl-4-(1H-2-pyridon-1-yl)-6-ethoxycarbonyl-chroman-3-ol
2,2,3-trimethyl-4-(1H-2-pyridon-1-yl)-6-fluoro-2H-chromene
2,2,3-trimethyl-4-(1H-2-pyridon-1-yl)-6-fluoro-chroman-3-ol
2,2,3-trimethyl-4-(1H-2-pyridon-1-yl)-6-chloro-2H-chromene
2,2,3-trimethyl-4-(1H-2-pyridon-1-yl)-6-chloro-chroman-3-ol
2,2,3-trimethyl-4-(1H-2-pyridon-1-yl)-6-trifluoromethyl-2H-chromene
2,2,3-trimethyl-4-(1H-2-pyridon-1-yl)-6-trifluoromethyl-chroman-3-ol
2,2,3-trimethyl-4-(1H-2-pyridon-1-yl)-6-acetamido-2H-chromene
2,2,3-trimethyl-4-(1H-2-pyridon-1-yl)-6-acetamido-chroman-3-ol
2,2,3-trimethyl-4-(1H-2-pyridon-1-yl)-6-carbamoyl-2H-chromene
2,2,3-trimethyl-4-(1H-2-pyridon-1-yl)-6-carbamoyl-chroman-3-ol
2,2,3-trimethyl-4-(1H-2-pyridon-1-yl)-6-thiocarbamoyl-2H-chromene
2,2,3-trimethyl-4-(1H-2-pyridon-1-yl)-6-thiocarbamoyl-chroman-3-ol
2,2,3-trimethyl-4-(1H-2-pyridon-1-yl)-7-cyano-2H-chromene
2,2,3-trimethyl-4-(1H-2-pyridon-1-yl)-7-cyano-chroman-3-ol
2,2,3-trimethyl-4-(1H-2-pyridon-1-yl)-6-acetamido-7-nitro-2H-chromene
2,2,3-trimethyl-4-(1H-2-pyridon-1-yl)-6-acetamido-7-nitro-chroman-3-ol
2,2,3-trimethyl-4-(1H-3-nitro-2-pyridon-1-yl)-6-methoxycarbonyl-2H-chromene
2,2,3-trimethyl-4-(1H-3-nitro-2-pyridon-1-yl)-6-methoxycarbonyl-chroman-3-ol
2,2-tetramethylene-3-methyl-4-(1H-2-pyridon-1-yl)-6-cyano-2H-chromene
2,2-tetramethylene-3-methyl-4-(1H-2-pyridon-1-yl)-6-cyano-chroman-3-ol 2,2-pentamethylene-3-methyl-4-(1H-2-pyridon-1-yl)-6-cyano-2H-chromene
2,2-pentamethylene-3-methyl-4-(1H-2-pyridon-1-yl)-6-cyano-chroman-3-ol, m.p. 204°–206°
2,2,3-trimethyl-4-(1H-6-pyridazinon-1-yl)-6-cyano-2H-chromene
2,2,3-trimethyl-4-(1H-6-pyridazinon-1-yl)-6-cyano-chroman-3-ol
2,2,3-trimethyl-4-(4,5-dihydro-1H-6-pyridazinon-1-yl)-6-cyano-2H-chromene
2,2,3-trimethyl-4-(4,5-dihydro-1H-6-pyridazinon-1-yl)-6-cyano-chroman-3-ol
2,2,3-trimethyl-4-(1H-3-hydroxy-6-pyridazinon-1-yl)-6-cyano-2H-chromene
2,2,3-trimethyl-4-(1H-3-hydroxy-6-pyridazinon-1-yl)-6-cyano-chroman-3-ol
2,2,3-trimethyl-4-(1H-3-amino-6-pyridazinon-1-yl)-6-cyano-chroman-3-ol, m.p. 239°–242°
2,2,3-trimethyl-4-(1H-3-ethoxycarbonyl-6-pyridazinon-1-yl)-6-cyano-chroman-3-ol
2,2,3-trimethyl-4-(1H-2-pyrimidinon-1-yl)-6-cyano-2H-chromene
2,2,3-trimethyl-4-(1H-2-pyrimidinon-1-yl)-6-cyano-chroman-3-ol
2,2,3-trimethyl-4-(1H-4-hydroxy-2-pyrimidinon-1-yl)-6-cyano-2H-chromene
2,2,3-trimethyl-4-(1H-4-hydroxy-2-pyrimidinon-1-yl)-6-cyano-chroman-3-ol
2,2,3-trimethyl-4-(1H-6-pyrimidinon-1-yl)-6-cyano-2H-chromene
2,2,3-trimethyl-4-(1H-6-pyrimidinon-1-yl)-6-cyano-chroman-3-ol
2,2,3-trimethyl-4-(1H-4-hydroxy-6-pyrimidinon-1-yl)-6-cyano-2H-chromene
2,2,3-trimethyl-4-(1H-4-hydroxy-6-pyrimidinon-1-yl)-6-cyano-chroman-3-ol
2,2,3-trimethyl-4-(1H-2-pyrazinon-1-yl)-6-cyano-2H-chromene
2,2,3-trimethyl-4-(1H-2-pyrazinon-1-yl)-6-cyano-chroman-3-ol
2,2,3-trimethyl-4-(2-pyrrolidon-1-yl)-6-cyano-2H-chromene, m.p. 186°
2,2,3-trimethyl-4-(2-pyrrolidon-1-yl)-6-cyano-chroman-3-ol, m.p. 195°–197°
2,2,3-trimethyl-4-(2-piperidinon-1-yl)-6-cyano-2H-chromene
2,2,3-trimethyl-4-(2-piperidinon-1-yl)-6-cyano-chroman-3-ol
2,2-dimethyl-3-ethyl-4-(1H-2-pyridon-1-yl)-6-cyano-2H-chromene
2,2-dimethyl-3-ethyl-4-(1H-2-pyridon-1-yl)-6-cyano-chroman-3-ol.

EXAMPLE 2

A mixture of 21.5 g of IIa, 11.2 g of 3,6-pyridazinediol, 12 ml of pyridine and 600 ml of ethanol is boiled for 72 hours. About 300 ml of solvent is distilled off, the mixture is cooled, unreacted 3,6-pyridazinediol is filtered off and the filtrate is evaporated. The 2,2,3-trimethyl-4-(6-hydroxy-3-pyridazinyl-oxy)-6-cyano-chroman-3-ol [=2,2,3-Trimethyl-4-(1,6-dihydro-6-oxo-3-pyridazinyl-oxy)-6-cyano-chroman-3-ol] obtained is recrystallized from isopropanol. m.p. 240°.

The following are obtained analogously from the corresponding 3,4-epoxychromans:
2,3-dimethyl-4-(6-hydroxy-3-pyridazinyl-oxy)-chroman-3-ol
2,3-dimethyl-4-(6-hydroxy-3-pyridazinyl-oxy)-6-cyano-chroman-3-ol
2,3-dimethyl-4-(6-hydroxy-3-pyridazinyl-oxy)-6-nitro-chroman-3-ol
2,3-dimethyl-2-ethyl-4-(6-hydroxy-3-pyridazinyl-oxy)-6-cyano-chroman-3-ol
2,2-diethyl-3-methyl-4-(6-hydroxy-3-pyridazinyl-oxy)-6-cyano-chroman-3-ol
2,2-trimethylene-3-methyl-4-(6-hydroxy-3-pyridazinyl-oxy)-6-cyano-chroman-3-ol
2,2-hexamethylene-3-methyl-4-(6-hydroxy-3-pyridazinyl-oxy)-6-cyano-chroman-3-ol
2,2,3-trimethyl-4-(6-hydroxy-3-pyridazinyl-oxy)-chroman-3-ol
2,2,3-trimethyl-4-(6-hydroxy-3-pyridazinyl-oxy)-6-methyl-chroman-3-ol
2,2,3-trimethyl-4-(6-hydroxy-3-pyridazinyl-oxy)-6-methoxy-chroman-3-ol
2,2,3-trimethyl-4-(6-hydroxy-3-pyridazinyl-oxy)-6-thioacetyl-chroman-3-ol
2,2,3-trimethyl-4-(6-hydroxy-3-pyridazinyl-oxy)-6-methoxy-thiocarbonyl-chroman-3-ol
2,2,3-trimethyl-4-(6-hydroxy-3-pyridazinyl-oxy)-6-thio(no)acetoxy-chroman-3-ol
2,2,3-trimethyl-4-(6-hydroxy-3-pyridazinyl-oxy)-6-hydroxymethyl-chroman-3-ol
2,2,3-trimethyl-4-(6-hydroxy-3-pyridazinyl-oxy)-6-dimethylamino-chroman-3-ol
2,2,3-trimethyl-4-(6-hydroxy-3-pyridazinyl-oxy)-6-bromo-chroman-3-ol
2,2,3-trimethyl-4-(6-hydroxy-3-pyridazinyl-oxy)-6-iodo-chroman-3-ol
2,2,3-trimethyl-4-(6-hydroxy-3-pyridazinyl-oxy)-6-methylsulfinyl-chroman-3-ol
2,2,3-trimethyl-4-(6-hydroxy-3-pyridazinyl-oxy)-6-methylsulfonyl-chroman-3-ol
2,2-dimethyl-3-hexyl-4-(6-hydroxy-3-pyridazinyl-oxy)-6-cyano-chroman-3-ol.

EXAMPLE 3

A mixture of 10 g of "B", 3 g of sodium hydroxide and 350 ml of dioxane is boiled for 20 min. The mixture is cooled, filtered, and the filtrate is evaporated and "A" is obtained, m.p. 212°.

EXAMPLE 4

A mixture of 2 g of "B", 11.7 ml of formic acid and 3.3 ml of acetic anhydride is allowed to stand at 20° for 16 hours and subsequently heated at 40°–42° for 2 hours. After evaporating and customary working up, 2,2,3-trimethyl-3-formyloxy-4-(1H-2-pyridon-1-yl)-6-cyano-chroman is obtained.

The following are obtained analogously from the corresponding 3-hydroxy-chromans:
2,2,3-trimethyl-3-formyloxy-4-(1H-2-pyridon-1-yl)-6-nitro-chroman
2,2,3-trimethyl-3-formyloxy-4-(1H-4-hydroxy-2-pyridon-1-yl)-6-cyano-chroman
2,2,3-trimethyl-3-formyloxy-4-(1H-3-hydroxy-6-pyridazinon-1-yl)-6-cyano-chroman.

EXAMPLE 5

A mixture of 1 g of "B" and 5 ml of acetic anhydride is boiled for 1 hour. The mixture is cooled, worked up as usual and 2,2,3-trimethyl-3-acetoxy-4-(1H-2-pyridon-1-yl)-6-cyano-chroman is obtained.

EXAMPLE 6

2.96 g of "B" are suspended in 100 ml of water and 3.2 g of bromine are added dropwise with stirring at 10°-20°. The substance dissolves and 2,2,3-trimethyl-4-(1H-3,5-dibromo-2-pyridon-1-yl)-6-cyano-chroman-3-ol precipitates and is filtered off.

EXAMPLE 7

2.78 g of "A" are dissolved in a mixture of 10 ml of concentrated nitric acid (68%; density 1.41) and 12 ml of concentrated sulfuric acid, stirred at 20° for 3 hours and poured onto ice, the precipitate is filtered and washed with water, and a mixture of 2,2,3-trimethyl-4-(1H-3-and -5-nitro-pyridon-1-yl)-6-cyano-2H-chromene is obtained, which can be separated chromatographically.

EXAMPLE 8

A solution of 1 g of 2,2,3-trimethyl-4-(1H-3-nitro-2-pyridon-1-yl)-6-methoxycarbonyl-chroman-3-ol in 25 ml of methanol is hydrogenated to completion at 20° and 1 bar on 0.5 g of 5% Pd-C. The mixture is filtered, the filtrate is evaporated and 2,2,3-trimethyl-4-(1H-3-amino-2-pyridon-1-yl)-6-methoxycarbonyl-chroman-3-ol is obtained.

EXAMPLE 9

A solution of 1 g of 2,2,3-trimethyl-4-(1H-3-amino-2-pyridon-1-yl)-6-cyano-2H-chromene in 15 ml of HCOOH and 1 ml of pyridine is boiled for 19 hours and evaporated. After customary working up, 2,2,3-trimethyl-4-(1H-3-formamido-2-pyridon-1-yl)-6-cyano-2H-chromene is obtained.

EXAMPLE 10

A mixture of 1 g of 2,2,3-trimethyl-4-(1H-5-amino-2-pyridon-1-yl)-6-cyano-2H-chromene, 10 ml of acetic anhydride and 10 ml of pyridine is allowed to stand at 20° for 16 hours. The mixture is evaporated, the residue is purified chromatographically and 2,2,3-trimethyl-4-(1H-5-acetamido-2-pyridon-1-yl)-6-cyano-2H-chromene is obtained.

EXAMPLE 11

HCl is passed into a boiling solution of 1 g of "A" in 50 ml of methanol and 2 ml of water with stirring for 14 hours. The mixture is allowed to cool and to stand overnight. The precipitated 2,2,3-trimethyl-4-(1H-2-pyridon-1-yl)-2H-chromene-6-carboxylic acid is filtered off.

EXAMPLE 12

A mixture of 2.78 g of "A", 31 g of $Na_3PO_4.12H_2O$, 28 ml of pyridine, 28 ml of water, 67 ml of acetic acid and 25 g of Raney Ni (moistened with water) is stirred at 20° for 3 hours. After filtering, customary working up gives 2,2,3-trimethyl-4-(1H-2-pyridon-1-yl)-6-formyl-2H-chromene.

The following are obtained analogously
2,2,3-trimethyl-4-(1H-2-pyridon-1-yl)-6-formyl-chroman-3-ol
2,2,3-trimethyl-4-(1H-2-pyridon-1-yl)-7-formyl-2H-chromene
2,2,3-trimethyl-4-(1H-2-pyridon-1-yl)-7-formyl-chroman-3-ol
2,2,3-trimethyl-4-(1H-4-hydroxy-2-pyridon-1-yl)-6-formyl-2H-chromene
2,2,3-trimethyl-4-(1H-4-hydroxy-2-pyridon-1-yl)-6-formyl-chroman-3-ol
2,2,3-trimethyl-4-(1H-3-hydroxy-6-pyridazinon-1-yl)-6-formyl-2H-chromene
2,2,3-trimethyl-4-(1H-3-hydroxy-6-pyridazinon-1-yl)-6-formyl-chroman-3-ol.

EXAMPLE 13

2.78 g of "A" are dissolved in 40 ml of tert.-butanol and 5.6 g of powdered KOH are added with stirring. After boiling for 1 hour and customary working up, 2,2,3-trimethyl-4-(1H-2-pyridon-1-yl)-6-carbamoyl-2H-chromene is obtained.

The following are obtained analogously
2,2,3-trimethyl-4-(1H-2-pyridon-1-yl)-6-carbamoyl-chroman-3-ol
2,2,3-trimethyl-4-(1H-2-pyridon-1-yl)-7-carbamoyl-2H-chromene
2,2,3-trimethyl-4-(1H-2-pyridon-1-yl)-7-carbamoyl-chroman-3-ol
2,2,3-trimethyl-4-(1H-4-hydroxy-2-pyridon-1-yl)-6-carbamoyl-2H-chromene
2,2,3-trimethyl-4-(1H-4-hydroxy-2-pyridon-1-yl)-6-carbamoyl-chroman-3-ol
2,2,3-trimethyl-4-(1H-3-hydroxy-6-pyridazinon-1-yl)-6-carbamoyl-2H-chromene
2,2,3-trimethyl-4-(1H-3-hydroxy-6-pyridazinon-1-yl)-6-carbamoyl-chroman-3-ol.

EXAMPLE 14

$H_2S$ is passed into a solution of 2.78 g of "A" in a mixture of 20 ml of pyridine and 10 ml of triethylamine at 20° for 5 hours, the mixture is evaporated and worked up as usual, and 2,2,3-trimethyl-4-(1H-2-pyridon-1-yl)-6-thiocarbamoyl-2H-chromene is obtained.

The following are obtained analogously
2,2,3-trimethyl-4-(1H-2-pyridon-1-yl)-6-thiocarbamoyl-chroman-3-ol
2,2,3-trimethyl-4-(1H-2-pyridon-1-yl)-7-thiocarbamoyl-2H-chromene
2,2,3-trimethyl-4-(1H-2-pyridon-1-yl)-7-thiocarbamoyl-chroman-3-ol
2,2,3-trimethyl-4-(1H-4-hydroxy-2-pyridon-1-yl)-6-thiocarbamoyl-2H-chromene
2,2,3-trimethyl-4-(1H-4-hydroxy-2-pyridon-1-yl)-6-thiocarbamoyl-chroman-3-ol
2,2,3-trimethyl-4-(1H-3-hydroxy-6-pyridazinon-1-yl)-6-thiocarbamoyl-2H-chromene
2,2,3-trimethyl-4-(1H-3-hydroxy-6-pyridazinon-1-yl)-6-thiocarbamoyl-chroman-3-ol.

EXAMPLE 15

A mixture of 310 mg of "B", 808 mg of Lawesson reagent and 50 ml of toluene is boiled under $N_2$ for 1 hour. Customary working up gives 2,2,3-trimethyl-4-(1H-2-thiopyridon-1-yl)-6-cyano-chroman-3-ol.

2,2,3-Trimethyl-4-(1H-2-thiopyridon-1-yl)-6-cyano-2H-chromene is obtained analogously from "A".

EXAMPLE 16

The following are obtained analogously to Example 1:
2,2,3-trimethyl-4-(1H-4-methoxy-2-pyridon-1-yl)-6-cyano-2H-chromene
2,2,3-trimethyl-4-(1H-4-methoxy-2-pyridon-1-yl)-6-cyano-chroman-3-ol
2,2,3-trimethyl-4-(1H-4-ethoxy-2-pyridon-1-yl)-6-cyano-2H-chromene 2,2,3-trimethyl-4-(1H-4-ethoxy-2-pyridon-1-yl)-6-cyano-chroman-3-ol
2,2,3-trimethyl-4-(1H-4-acetoxy-2-pyridon-1-yl)-6-cyano-2H-chromene
2,2,3-trimethyl-4-(1H-4-acetoxy-2-pyridon-1-yl)-6-cyano-chroman-3-ol
2,2,3-trimethyl-4-(1H-2-pyridon-1-yl)-6-cyano-8-nitro-2H-chromene
2,2,3-trimethyl-4-(1H-2-pyridon-1-yl)-6-cyano-8-nitro-chroman-3-ol
2,2,3-trimethyl-4-(1H-2-pyridon-1-yl)-6-hydroxymethyl-2H-chromene
2,2,3-trimethyl-4-(1H-2-pyridon-1-yl)-6-hydroxymethyl-chroman-3-ol
2,2-tetramethylene-3-methyl-4-(1H-2-pyridon-1-yl)-6-nitro-2H-chromene
2,2-tetramethylene-3-methyl-4-(1H-2-pyridon-1-yl)-6-nitro-chroman-3-ol
2,2-pentamethylene-3-methyl-(1H-2-pyridon-1-yl)-6-nitro-2H-chromene
2,2-pentamethylene-3-methyl-4-(1H-2-pyridon-1-yl)-6-nitro-chroman-3-ol
2,2,3-trimethyl-4-(1H-3-methoxy-6-pyridazinon-1-yl)-6-cyano-2H-chromene
2,2,3-trimethyl-4-(1H-3-methoxy-6-pyridazinon-1-yl)-6-cyano-chroman-3-ol
2,2,3-trimethyl-4-(1H-4-hydroxy-2-pyridon-1-yl)-6-acetyl-2H-chromene
2,2,3-trimethyl-4-(1H-4-hydroxy-2-pyridon-1-yl)-6-acetyl-chroman-3-ol
2,2,3-trimethyl-4-(1H-4-hydroxy-2-pyridon-1-yl)-6-methoxycarbonyl-2H-chromene
2,2,3-trimethyl-4-(1H-4-hydroxy-2-pyridon-1-yl)-6-methoxycarbonyl-chroman-3-ol
2,2,3-trimethyl-4-(1H-4-hydroxy-2-pyridon-1-yl)-6-ethoxycarbonyl-2H-chromene
2,2,3-trimethyl-4-(1H-4-hydroxy-2-pyridon-1-yl)-6-ethoxycarbonyl-chroman-3-ol
2,2,3-trimethyl-4-(1H-3-hydroxy-6-pyridazinon-1-yl)-6-acetyl-2H-chromene
2,2,3-trimethyl-4-(1H-3-hydroxy-6-pyridazinon-1-yl)-6-acetyl-chroman-3-ol
2,2,3-trimethyl-4-(1H-3-hydroxy-6-pyridazinon-1-yl)-6-methoxycarbonyl-2H-chromene
2,2,3-trimethyl-4-(1H-3-hydroxy-6-pyridazinon-1-yl)-6-methoxycarbonyl-chroman-3-ol
2,2,3-trimethyl-4-(1H-3-hydroxy-6-pyridazinon-1-yl)-6-ethoxycarbonyl-2H-chromene
2,2,3-trimethyl-4-(1H-3-hydroxy-6-pyridazinon-1-yl)-6-ethoxycarbonyl-chroman-3-ol
2,2,3-trimethyl-4-(1H-3-hydroxy-6-pyridazinon-1-yl)-6-nitro-2H-chromene
2,2,3-trimethyl-4-(1H-3-hydroxy-6-pyridazinon-1-yl)-6-nitro-chroman-3-ol.

EXAMPLE 17

A mixture of 6.5 g of IIa, 3.1 g of pyridone, 3 ml of pyridine and 100 ml of ethanol is refluxed for 72 hours. After cooling and working up as usual, the mixture is chromatographed over silica gel. There is eluted with dichloromethane/petroleum ether (85:15) 2,2,3-trimethyl-4-(2-pyridyl-oxy)-6-cyano-chroman-3-ol (m.p. 105°–107°) subsequently with dichloromethane/ethyl acetate (85:15) "B", m.p. 185°–186°; weight ration about 1:1.

EXAMPLE 18

A mixture of 21.5 g of IIa, 11.1 g of 2,4-dihydroxypyridine (=4-hydroxy-1H-2-pyridinone), 12 ml of pyridine and 360 ml of ethanol is refluxed for 48 hours. After cooling and working up as usual, the mixture is chromatographed over silica gel. 2,2,3-Trimethyl-4-(4-hydroxy-1H-2-pyridon-1-yl)-6-cyano-chroman-3-ol (m.p. 225°–227°) is eluted with dichloromethane/ethyl acetate (85:15), followed by 2,2,3-trimethyl-4-(1,2-dihydro-2-oxo-4-pyridyl-oxy)-6-cyano-chroman-3-ol [2,2,3-trimethyl-4-(2-hydroxy-4-pyridyl-oxy)-6-cyano-chroman-3-ol, F. 198°–200°, m.p. 198°–200°], with ethyl acetate/methanol (90:10); weight ratio about 1:9.

EXAMPLE 19

Analogously to Example 2, there are obtained from IIa or from the corresponding 2,2,3-trimethyl-3,4-epoxy-chromanes with 3-hydroxypyridine:
2,2,3-trimethyl-4-(3-pyridyl-oxy)-6-cyano-chroman-3-ol;
with 4-hydroxypyridine:
2,2,3-trimethyl-4-(4-pyridyl-oxy)-6-cyano-chroman-3-ol;
with 3-hydroxypyridazine:
2,2,3-trimethyl-4-(3-pyridazinyl-oxy)-6-cyano-chroman-3-ol;
with 4-hydroxypyrimidine:
2,2,3-trimethyl-4-(3-pyrimidinyl-oxy)-6-cyano-chroman-3-ol;
with 2-hydroxypyrazine:
2,2,3-trimethyl-4-(2-pyrazinyl-oxy)-6-cyano-chroman-3-ol;
with 2,4-dihydroxypyridine:
2,2,3-trimethyl-4-(2-hydroxy-4-pyridyl-oxy)-6-nitro-chroman-3-ol
2,2,3-trimethyl-4-(2-hydroxy-4-pyridyl-oxy)-6-bromo-chroman-3-ol
2,2,3-trimethyl-4-(2-hydroxy-4-pyridyl-oxy)-6-methoxycarbonyl-chroman-3-ol;
with 2,3-dihydroxypyridine:
2,2,3-trimethyl-4-(2-hydroxy-3-pyridyl-oxy)-6-cyano-chroman-3-ol;
with 2,5-dihydroxypyridine:
2,2,3-trimethyl-4-(2-hydroxy-5-pyridyl-oxy)-6-cyano-chroman-3-ol;
with 4,6-dihydroxypyrimidine:
2,2,3-trimethyl-4-(6-hydroxy-4-pyrimidinyl-oxy)-6-cyano-chroman-3-ol;
with 3,6-dihydroxypyridazine:
2,2,3-trimethyl-4-(6-hydroxy-3-pyridazinyl-oxy)-6-nitro-chroman-3-ol, m.p. 223°–225°
2,2-tetramethylen-3-methyl-4-(6-hydroxy-3-pyridazinyl-oxy)-6-cyano-chroman-3-ol
2,2-pentamethylen-3-methyl-4-(6-hydroxy-3-pyridazinyl-oxy)-6-cyano-chroman-3-ol, no m.p. until 275°
2,2,3-trimethyl-4-(6-hydroxy-3-pyridazinyl-oxy)-6-bromo-chroman-3-ol
2,2,3-trimethyl-4-(6-hydroxy-3-pyridazinyl-oxy)-6-methoxycarbonyl-chroman-3-ol.

EXAMPLE 20

Analogously to Example 4, there are obtained by formylation of the corresponding chroman-3-ols:
2,2,3-trimethyl-3-formyloxy-4-(6-hydroxy-3-pyridazinyl-oxy)-6-cyano-chromane 2,2,3-trimethyl-3-formyloxy-4-(2-hydroxy-4-pyridyl-oxy)-6-cyano-chromane.

EXAMPLE 21

Analogously to Example 5, these are obtained by acetylation of the corresponding chroman-3-ols;
2,2,3-trimethyl-6-acetoxy-4-(6-hydroxy-3-pyridazinyl-oxy)-6-cyano-chromane
2,2,3-trimethyl-6-acetoxy-4-(2-hydroxy-4-pyridyl-oxy)-6-cyano-chromane.

EXAMPLE 22

A mixture of 327 mg of 2,2,3-trimethyl-4-(1,6-dihydro-6-oxo-3-pyridazinyl-oxy)-6-cyano-chroman-3-ol, 20 ml of acetone, 400 mg of $K_2CO_3$ and 0.2 ml of dimethyl sulfate is refluxed for 2 hours. The mixture is filtered, concentrated and chromatographed on silica gel. There is obtained with ethyl acetate/methanol (9:1) 2,2,3-trimethyl-4-(1,6-dihydro-1-methyl-6-oxo-3-pyridazinyl-oxy)-6-cyano-chroman-3-ol, m.p. 197°–199°.

Analogously, there are obtained by alkylation:
2,2,3-trimethyl-4-(1,2-dihydro-1-methyl-2-oxo-4-pyridyl-oxy)-6-cyano-chroman-3-ol
2,2,3-trimethyl-4-(1,2-dihydro-1-ethyl-2-oxo-4-pyridyl-oxy)-6-cyano-chroman-3-ol
2,2,3-trimethyl-4-(1,6-dihydro-1-ethyl-6-oxo-3-pyridazinyl-oxy)-6-cyano-chroman-3-ol, m.p. 166°–168°.

The examples below relate to pharmaceutical preparations which contain the compounds of the formula I or their physiologically acceptable salts:

EXAMPLE A

Tablets

A mixture of 1 kg of 2,2,3-trimethyl-4-(1H-2-pyridon-1-yl)-6-cyano-2H-chromene, 4 kg of lactose, 1.2 kg of potato starch, 0.2 g of talc and 0.1 kg of magnesium stearate is pressed to give tablets in a customary manner, in such a way that each tablet contains 0.1 mg of active compound.

EXAMPLE B

Coated tablets

Tablets are pressed analogously to Example A, and are subsequently coated in a customary manner with a coating of sucrose, potato starch, talc, tragacanth and colorant.

EXAMPLE C

Capsules

Hard gelatin capsules are filled in a customary manner with 1 kg of 2,2,3-trimethyl-4-(6-hydroxy-3-pyridazinyl-oxy)-6-cyano-chroman-3-ol so that each capsule contains 0.5 mg of active compound.

EXAMPLE D

Ampoules

A solution of 1 kg of 2,2,3-trimethyl-4-(2-hydroxy-4-pyridyl-oxy)-6-cyano-chroman-3-ol in a mixture of 20 l of 1,2-propanediol and 10 l of double-distilled water is sterile filtered, the solution is filled into ampoules and the ampoules are sealed in a sterile manner. Each ampoule contains 0.1 mg of active compound.

Analogously, tablets, dragees, capsules or ampoules are obtainable which contain one or more of the other active compounds of the formula I and/or their physiologically acceptable salts.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make varoius changes and modifications of the invention and adapt it to various usagess and conditions.

What is claimed is:

1. A compound of the formula

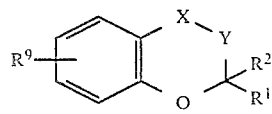

wherein
—X—Y— is (a) —CO—CR$^{10}$—, or (b) —CH=C-R$^8$—
R$^9$ is CHO, ACO, AOOC, NO$_2$, CN, Br, H$_2$NCO or H$_2$NCS,
A is alkyl having 1–6 carbon atoms,
R$^{10}$ is alkylidene having 1–6 C atoms,
R$^1$ and R$^8$ are in each case independently A,
R$^2$ is H or A, or
R$^1$ and R$^2$ together are alkylene having 3–6 C atoms.

2. 2,2-dimethyl-3-methylene-6-cyano-4-chromanone, a compound of claim 1.

3. A compound of claim 1, wherein —X—Y— is —CO—CR$^{10}$—.

4. A compound of claim 1, wherein R$^8$ is C$_{1-3}$-alkyl.

* * * * *